United States Patent [19]

Sage

[11] Patent Number: 5,616,850
[45] Date of Patent: Apr. 1, 1997

[54] EMISSIONS MEASURING SYSTEM AND METHOD

[75] Inventor: Gerald F. Sage, Mountain View, Calif.

[73] Assignee: Gas Research Institute, Chicago, Ill.

[21] Appl. No.: 580,710

[22] Filed: Dec. 29, 1995

[51] Int. Cl.$^6$ .................................................. G01N 7/00
[52] U.S. Cl. ............................................ 73/23.31; 422/95
[58] Field of Search ............................ 73/23.31, 25.01, 73/25.05; 422/94, 95, 98

[56] References Cited

U.S. PATENT DOCUMENTS

| | | | |
|---|---|---|---|
| 2,782,102 | 2/1957 | Howe | 73/23.31 |
| 4,528,637 | 7/1985 | Smith | 364/557 |
| 4,738,147 | 4/1988 | Tomlin | 73/864 |
| 4,974,455 | 12/1990 | McGowan et al. | 73/863 |
| 5,237,881 | 8/1993 | Ross | 73/863 |
| 5,285,053 | 2/1994 | Fowler | 219/506 |
| 5,317,520 | 5/1994 | Castle | 364/482 |
| 5,360,266 | 11/1994 | Lenfers et al. | 73/23.31 X |
| 5,423,228 | 6/1995 | Budd et al. | 73/863 |

*Primary Examiner*—Hezron E. Williams
*Assistant Examiner*—Jay L. Politzer
*Attorney, Agent, or Firm*—Thomas, Kayden, Horstemeyer & Risley

[57] ABSTRACT

A measuring system for use in an emissions monitor and comprising a control mechanism (12) and a sensor mechanism (14). The control mechanism (12) means a differential current passing through an active resistive temperature device RTD (34) with respect to the current flowing through a reference RTD (36) when the sensor mechanism (14) is exposed to a particular gas of interest. The differential current is detected by control mechanism (12) via a four winding transformer (32) having an active winding (A), a reference winding (R), a sense winding (S), and a zero winding (Z). The current delivered to the active RTD (34) passes through the active winding (A) while the current passing through the reference RTD (36) passes through the reference winding (R) so as to produce a differential flux in the core of the transformer (32). The differential flux is detected by the sense winding (S) and is converted into a voltage signal by a current-to-voltage convertor (42). The voltage signal is subsequently converted by an analog-to-digital convertor (44) into a digital signal that is processed by a processor (48). The processor (48) applies a PID algorithm to the digital values in order to derive a control signal proportional to the concentration of the particular gas detected by the sensor mechanism (14). The control signal is combined with the excitation signal generated by the oscillator (20) at a multiplying DAC (28) in order to generate a precision zero signal which is sent to the zero winding (Z) in order to cancel the flux detected by sense winding (S).

20 Claims, 5 Drawing Sheets

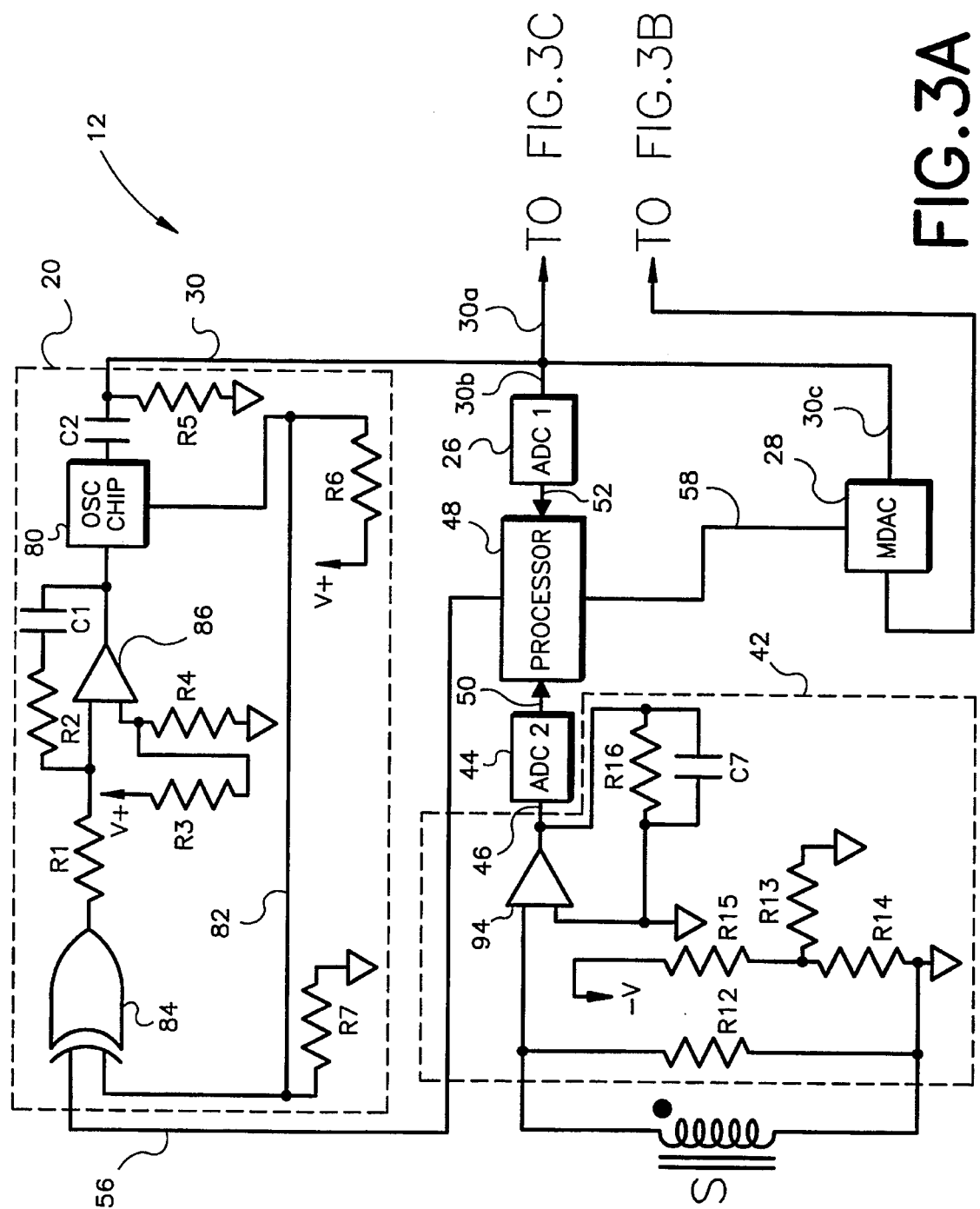

EMISSIONS MEASURING SYSTEM AND METHOD

FIELD OF THE INVENTION

The present invention generally relates to emissions monitoring systems for measuring the gaseous components in a gas sample extracted from the exhaust stream of an industrial process, and more particularly, to an emissions measuring system that utilizes resistive temperature devices and a nulling circuit to measure emissions over a wide range of values with accuracy.

BACKGROUND OF THE INVENTION

In accordance with the Clean Air Act, the amendments made thereto, and numerous other municipal, state and Federal laws and/or regulations, large scale industrial processing facilities are required to perform compliance monitoring of their emissions to ensure designated pollutant levels are not exceeded. Compliance monitoring is typically required to be performed on a continuous basis, but occasionally is only required on a periodic basis. In addition, emission monitoring is also performed as a process control measure for such purposes as evaluating combustion efficiency or fine tuning an emission clean-up scheme. Consequently, emissions monitoring plays an important role in protecting the health and welfare of the environment and in the efficient use of our natural resources as used in industrial operations.

In most industrial process facilities, the exhaust stack is positioned adjacent an emission source, such as a boiler, in order to receive and direct the process exhaust upwardly into the atmosphere. In order to measure specific components of the emissions in the process exhaust, a sample line typically draws a portion of the exhaust from the exhaust stack and delivers it to a monitoring facility where sensors measure the amount of specific pollutants comprising the exhaust. In this configuration, the sample line is typically heated to maintain the temperature of the emissions within a desired range.

At the monitoring facility, any one of numerous types of sensors may be utilized to measure the gaseous components of the exhaust. Typically, the sensors are constructed to measure a particular gas of interest, or target gas, such as carbon monoxide (CO) or nitrogen oxide (such as NO or $NO_2$, generically referred to hereinafter as $NO_x$).

An example of such a sensor is a catalytic heat-flux sensor which includes two probes, an active and a reference, which are exposed to a gas sample extracted from the exhaust stream. At the tip of each probe is a precision temperature detector that changes resistance with changes in temperature, hereinafter referred to as a resistive temperature device (RTD). The active probe is coated with a catalyst which selectively promotes an exothermic reaction with the target gas so that an amount of heat directly proportional to the concentration of the target gas is generated. By measuring the amount of heat produced; the concentration of the target gas in the sample taken from the exhaust stack can be determined. This is typically done by measuring the differential resistance between the active probe and reference probe. Such catalytic heat-flux sensors are commercially available from numerous manufactures such as Advanced Sensor Devices, Inc., Mountain View, Calif., U.S.A.

Associated with each sensor, as a part of an emissions measuring system, is a circuit for reading the changes in resistance and for processing that information into an actual measurement value having the appropriate measurement unit such as parts per million (ppm). In FIG. 1, a well known measuring system 1 utilizing a catalytic heat sensor 2 is illustrated. As shown, the catalytic heat sensor 2 comprises an active RTD sensor 3a and a reference RTD sensor 3b. The active RTD sensor is coated with a catalyst that reacts with a target gas of interest, causing its temperature to rise when exposed to the target gas, and thereby, causing the resistance of the active RTD 3a to increase a proportional amount. Since the active and reference RTDs 3a, 3b are configured in parallel, an increase in resistance of the active RTD 3a causes the excitation signal from an oscillator 4 to be unequally divided between the active and reference RTDs 3a, 3b. Specifically, the current passing through the active RTD 3a and an active winding 5 differs from that passing through the reference RTD 3b and a reference winding 6. The different currents passing through the respective windings 5, causes a differential flux in the core of a transformer 7, which is detected by a sense winding 8. A current associated with the differential flux is converted by a conversion circuit 9 into a voltage signal which is proportional to the amount of gas detected by the catalytic heat sensor 2.

However, there are several inaccuracies built into such a circuit. For instance, transformers have an inherent non-linearity in their operation which results in varied performance throughout the range of currents that are applied to the transformer's windings. For example, a change in the differential current between active winding 5 and reference winding 6 does not produce an exactly corresponding change in the current in the sense winding 8 due to the non-linearity of the magnets of transformer 7. Moreover, the greater the current differential, the greater the effect of the non-linearity. This essentially reduces the range of valves for which the measuring system can accurately read.

In addition, the configuration shown in FIG. 1 utilizes a bridge circuit at the sensor in order to maintain a constant voltage across the active and reference RTD sensors 3a, 3b. Consequently, nulling must be performed in order to calibrate the active and reference RTD sensors 3a, 3b to account for manufacturing errors. Typically, this is accomplished by providing a direct current (d.c.) offset via an op amp (not shown) that is incorporated into the conversion circuit 9. This has proven to be an inaccurate and inefficient manner of nulling the sensor 2 because the practical implementation of a variable d.c. offset is inherently inaccurate, and further, because commercially available potentiometers lack sufficiently low temperature coefficients to accurately null the circuit over the normal range of operating temperatures.

Lastly, the electric components implementing the measuring system of FIG. 1 introduce drift into the circuits as a function of the change in environmental temperature and component aging. For example, the conversion 9 usually contains an amplifier whose gain changes with component valves. Thus, the output reading will change with changes in the gain, and therefore, producing an erroneous reading.

Hence, a heretofore unaddressed need exists in the industry for an emissions measuring system for use in emission monitoring that is capable of accurately measuring a wide range of concentration levels, with high sensitivity and low drift.

SUMMARY OF THE INVENTION

An object of the present invention is to overcome the deficiencies and inadequacies in the prior art as described above and as generally known in the industry.

Another object of the present invention is to provide a measuring system for accurately measuring process emissions over a wide range of values.

Another object of the present invention is to provide an emissions measuring system for accurately measuring process emissions over a period of time by improving the signal to noise ratio and reducing drift in the measuring system.

Another object of the present invention is to provide an emissions measuring system capable of accurately measuring process emissions with a poorly mismatched resistive temperature device pair.

Another object of the present invention is to provide an emissions measuring system capable of being remotely located with respect to an associated sensor.

Another object of the present invention is to provide an emissions measuring system that is insensitive to electrical noise, such as EMF and RFI noise, found at most industrial facilities.

Another object of the present invention is to provide an emissions measuring system in which multiple sensors share various electrical components in order to simplify implementation and overall cost, in addition to enabling more efficient modifications and/or changes.

Briefly stated, the present invention is an emissions measuring system that measures particular gaseous components in a gas sample extracted from the exhaust stream of an industrial process in order to compile historical records of particular gaseous emissions for compliance with EPA regulations and/or in order to monitor the efficiency of the process itself. The measurement system comprises a sensor mechanism located at the exhaust stack of the process and a control mechanism remotely located with respect to the sensor mechanism, typically at ground level, mounted to, or within close proximity of, the exhaust stack.

The sensor mechanism comprises a catalytic heat-flux sensor having an active resistive temperature device (RTD) and a reference RTD. The resistance of the active and reference RTDs are matched so that as the temperature of the exhaust varies, the resistances of the active and reference RTDs vary accordingly, but remain substantially equal to one another. The active RTD is further configured such that its temperature, and therefore its resistance, varies proportionally with the amount of a particular gas of interest to which it is exposed, as described above in the Background section. The resistance of reference RTD, on the other hand, does not change in response to exposure to the gasses in the exhaust. Thus, when the sensor is exposed to the target gas to which it is tuned (i.e., the target gas), the resistance of the active RTD is different from the resistance of the reference RTD. This differential resistance is measured by maintaining constant voltages across the active and reference RTDs, respectively, and measuring the currents through the active RTD and the reference RTD, respectively. The difference in the currents measured is indicative of the amount of the particular gas of interest to which the active RTD was exposed. This differential current is measured by the control mechanism.

The control mechanism measures the difference in the currents passing through the active and reference RTDs by generating a precisely known current (or control signal) that is equal to the differential current. The known current is indicative of the concentration of the target gas in the gas sample. The known current is digitally generated and is further processed into an actual measurement value having the appropriate units which can be sent to a user or stored on a memory device. The known current is also utilized after processing to null the field in a summing transformer of the control mechanism in order to eliminate sensitivity to the non-linearity and drift the control mechanism attributable to the system's hardware.

The control mechanism comprises a four winding transformer, an oscillator, a current-to-voltage (I-V) convertor, two analog-to-digital convertors (ADC), a processor, and a multiplying digital-to-analog convertor (DAC). The transformer includes an active winding connected to an active RTD of the sensor mechanism, a reference winding connected to a reference RTD of the sensor mechanism, a sense winding connected to the processor via the I-V converter and one of the ADCs, and a zero winding connected to the processor via the multiplying DAC. The oscillator provides an excitation signal to the active and reference windings of the transformer so that the currents through the respective windings produce cancelling fluxes. In operation, the current passing through the reference winding remains equal to the current through the active winding until the active RTD is exposed to the particular gas of interest. When exposed to the gas of interest, the catalyst on the active probe reacts with the target gas, generating heat which causes the resistance of the active RTD to differ from that of the reference RTD. Thus, because the voltage across each respective RTD remains constant, the current through the active RTD (and therefore, the active winding) varies with respect to the current that through the reference RTD (and therefore, the reference winding). The fluxes produced by the currents in the active and reference windings are designed to cancel one another, resulting in a differential flux if they are unequal. It should be noted that this differential or remaining flux may also be attributed, in part, to error in the control mechanism and/or sensor mechanism. The control mechanism generates and dynamically adjusts a precision zero current that is provided to the zero winding of the transformer to null the differential flux in the transformer.

A current associated with any remaining error flux is detected by the sense winding, and converted into a voltage signal by the current-to-voltage convertor. The voltage signal is further converted into a digital signal by one of the analog-to-digital convertors. The magnitude of the digital signal is indicative of the concentration of the target gas as sensed by the sensor mechanism. The digital signal is further processed by the processor via the application of a PID algorithm. The result of the PID algorithm is a control signal that is combined with other measured parameters and calibration factors to determine an actual measurement of the particular gas which is recorded on a memory device by the processor, and/or sent to be displayed on a display device for realtime evaluation.

In addition, the control signal is sent to the multiplying DAC. The multiplying DAC is utilized to generate the precision zero current, based on the control signal that is sent to the zero winding of the transformer in order to cancel out the differential flux detected by the sense winding. In addition to the control signal, the multiplying DAC receives the excitation signal from the oscillator which is proportionally reduced or scaled by the multiplying DAC in accordance with the magnitude of the control signal generated by the PID algorithm. Thus, the output of the multiplying DAC is a scaled portion of the oscillator excitation signal that is specifically engineered to cancel out any remaining differential flux in the transformer. By continuously nulling the flux in the transformer, the non-linearity and drift associated with the transformer is eliminated. In an ongoing fashion, changes in the concentration of the target gas at the sensor mechanism produce a change in the remaining flux, and thereby, resulting in an adjustment to the precision zero current delivered to the zero winding in order to null the flux in the transformer.

In order to allow the sensor mechanism to be remotely located with respect to the control mechanism, an active driver associated with the active winding and a reference driver associated with the reference winding are provided. The active and reference drivers supply a current boost to compensate for losses across the lead lines connecting the active and reference windings to the respective RTDs. In addition, the active driver and reference driver operate to maintain constant and equal voltages across the respective RTDs so that a change in the resistance of either RTD is reflected in a change in the current through the winding associated with that RTD.

In addition, a null driver is provided to receive the output of the multiplying DAC so that the appropriate precision zero current is provided to the zero winding. The null driver is configured in substantially the same as the active and reference drivers and generates a precision zero current proportional to the multiplying DAC output.

The present invention also provides for and can be conceptionalized as a method for measuring emissions of an industrial process comprising the following steps: (1) exposing a catalytic heat sensor to a gas sample extracted from an emissions exhaust stream of an industrial process, wherein the catalytic heat sensor includes an active RTD and a reference RTD; (2) measuring a first current through the active RTD and a second current through the reference RTD while maintaining constant and equal voltages across both the active and reference RTDs; (3) determining a differential current between the first and second measured currents by passing the currents through respective winding of a transformer having two opposing windings of a transformer such that a differential flux is produced in a sense winding of the transformer; (4) processing the differential flux as a current in order to generate a digital signal; (5) applying a PID algorithm to the digital signal in order to generate a control signal; (6) generating a precision nulling signal utilizing the control signal; (7) introducing the precision nulling signal to a zero winding of the transformer in order to cancel out the differential flux so as to eliminate the non-linearity and drift produced by the transformer; and (8) using the control signal to indicate the amount of emissions sensed by the catalytic heat sensor.

Other objects, features, and advantages of the present invention will become apparent to one skilled in the art upon examination of the following detailed description when considered in conjunction with the accompanying drawings. It is intended that all such additional objects, features, and advantages be included herein within the scope of the present invention, as defined by the appended claims.

BRIEF DESCRIPTION OF THE DRAWINGS

The present invention can be better understood with referenced to the following drawings. The elements of the drawings are not necessarily to scale, emphasis instead being placed upon clearly illustrating the principles of the present invention. Furthermore, like reference numerals designate corresponding pans throughout the several views.

FIGS. 3A, 3B and 3C is an illustrative embodiment of a circuit implementing the control mechanism of FIG. 2.

DETAILED DESCRIPTION OF THE PREFERRED EMBODIMENT

1. System Overview

Figure 1:
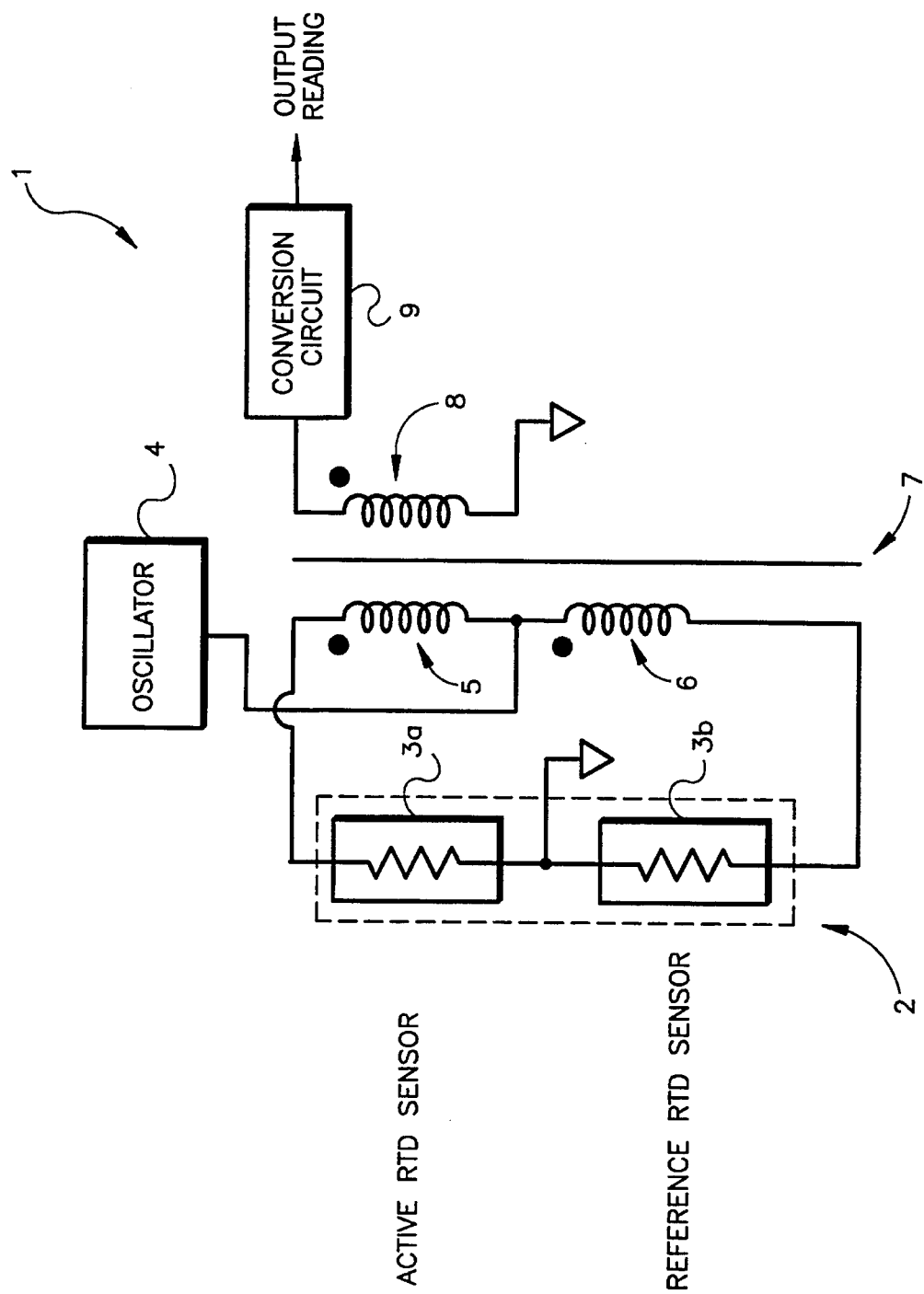
FIG. 1 is a block diagram of a prior art emissions measuring system.
Figure 2:
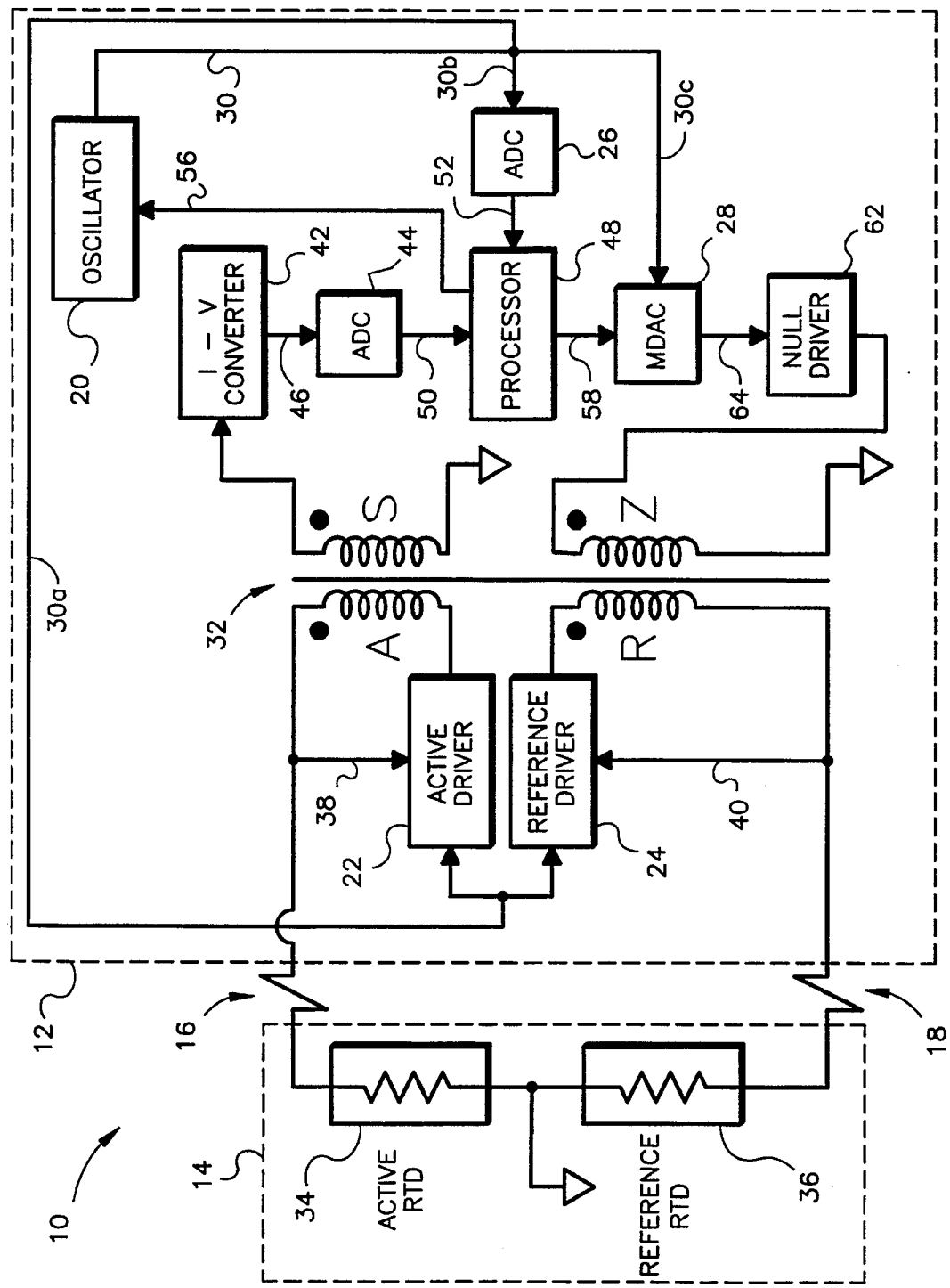
FIG. 2 is a block diagram of an emissions measuring system in accordance with the present invention.

With reference to FIG. 2, a block diagram of a measuring system 10 in accordance with the present invention is illustrated. As shown, the measuring system 10 includes a control mechanism 12 and a sensor mechanism 14. The control mechanism 12 and the sensor mechanism 14 are electrically connected via an active lead line 16 and a reference lead line 18. The lengths of lead lines 16 and 18 are substantially equal, and may vary from several feet up to 100 feet in length. Thus, in a preferred configuration, the sensor mechanism 14 can be located at a desirable position on the exhaust stack in order to measure emissions while the control mechanism 12 can be disposed at ground level or at a remote location with respect to the exhaust stack. Because the sensors are located at the exhaust stack, heated sample lines are not required in practicing the present invention.

The control mechanism 12 includes an oscillator 20 that provides an alternating current (a.c.) excitation signal to an active driver 22, a reference driver 24, a first analog-to-digital convertor (ADC) 26 and a multiplying digital-to-analog (DAC) convertor 28 over line 30. The excitation signal provided by the oscillator 20 is a stable signal of 4 volts peak-to-peak, preferably at a low frequency, for instance, 1 KHz.

The active driver 22 and reference driver 24 receive the excitation signal from the oscillator 20 via line 30a which branches off from line 30 and connects to the active driver 22 and the reference driver 24. The outputs of the active driver 22 and the reference driver 24 are coupled to respective windings of a four winding transformer 32.

The transformer 32 comprises an active winding A, a reference winding R, a sense winding S, and a zero winding Z. As indicated in FIG. 2, the output of the active driver 22 is connected to the active winding A and the output of the reference driver 24 is connected to the reference winding R. Because of the opposing senses of active winding A and reference winding R, the currents passing through the respective windings create fluxes having opposite senses which cancel one another, leaving only a differential flux in the core of transformer 32.

As indicated in FIG. 2, the currents passing through active winding A and reference winding R are sent to the sensor mechanism 14 across active lead line 16 and reference lead line 18, respectively.

The sensor mechanism 14 includes a catalytic heat sensor having an active RTD probe 34 and reference RTD probe 36. As previously discussed in the Background section, the active RTD 34 is coated with a catalysts which reacts with a particular gas of interest, referred to as the target gas. Because this reaction is exothermic, i.e., it produces an amount of heat that is directly proportional to the number of molecules of the target gas reacted, the temperature of the active RTD varies in accordance with the concentration of the target gas to which it is exposed. The reference RTD 36, however, is not coated with the catalysts so its temperature will not fluctuate because of exposure to the gases in the exhaust stream.

As well known in the industry and as discussed above, the resistance of an RTD device changes linearly in response changes in temperature, such as, 1 ohm for every 3° C. temperature swing. Accordingly, by monitoring the difference in resistance of the active RTD 34 with reference to the resistance of the reference RTD 36, the concentration of gas to which the active RTD 34 is exposed can be determined. In the preferred embodiment, a 100 ohm base RTD pair is preferred, such as the HES-$NO_x$ or HES-CO sensors manufactured by Advanced Sensor Devices, Inc., Mountain View, Calif., U.S.A.

The active driver 22 is configured to maintain a constant voltage across the active RTD 34. The active driver 22 controls the current delivered across active lead line 16 to the active RTD 34 so that changes in the resistance of the active RTD 34 can be adjusted for by a proportional change in the current delivered to active RTD 34. The voltage across active RTD 34 is monitored by a feedback line 38 that connects lead line 16 and active driver 22. Likewise, reference driver 24 is configured to maintain a constant voltage across the reference RTD 36 by providing proportional changes in the current delivered across reference lead line 18 to the reference RTD 36 as necessary to maintain a constant voltage on a feedback line 40 as the resistance of reference RTD 36 varies. Thus, as the resistances of the respective RTD change due to changes in exhaust temperature, changes in environmental temperatures, and, in the case of the active RTD 34, exposure to the target gas, appropriate changes in the amount of current delivered to the respective RTDs can be made by the associated driver. As evidence with reference to FIG. 2, a change in the amount of current delivered to either RTD results in a corresponding change in the current through the associated winding.

Typically, the currents through the active winding and reference winding are substantially the same when the active RTD is not exposed to the target. Thus, the fluxes produced by the respective windings are substantially equal and cancel one another out. However, there is usually some variations in the currents which can be attributed to component manufacturing error and/or component aging. These differences are accounted for during calibration of the measuring system.

Once the active RTD is exposed to a measurable amount of the particular gas of interest, the currents through the active winding and reference winding will differ. Thus, the fluxes produced by the respective windings will not be equal, generating a differential flux in the core of the transformer. In operation, a precision zero current is generated and sent to the zero winding Z to null this differential flux. The remaining flux in the core of transformer 32 from, for instance, subsequent variations in the differential flux is sensed by the sense winding S. The flux received by sense winding S produces a current which is delivered to a current-to-voltage (I-V) convertor 42. The voltage signal generated by the current-to-voltage convertor 42 is delivered to a second ADC 44 over line 46. The ADC 44 transforms the voltage signal into a digital signal that is sent to a processor 48 over line 50.

At the processor 48, a PID algorithm is applied to the digital signal in order to compute the required value of the precision zero current that sent to the zero winding Z to null the remaining differential flux. As commonly used in the industry, PID algorithms perform a control operation on the signal such that the output is proportional to a linear combination of the input signal, a time integral of the input signal, and a time rate-of-change of the input signal. Thus, the output is a proportional plus integral plus derivative function of the input signal, and therefore, is referred to by the acronym PID. In many practical applications, however, it may be desirable to disenable one or a combination of two of the operations in order to achieve a desired result. For example, the proportional and derivative PID operations may be disenabled and only the integral operation performed in order to provide desired smoothing operations on the input signal. However, it can be appreciated by one of ordinary skill in the art that numerous other processing operations other than PID may be applied to the digital signal to produce the desired results, such as with a filter algorithm.

As a novel feature of the present invention, the output of the PID algorithm, referred to hereafter as a control signal, is delivered to the multiplying DAC 28 as a reference signal via line 58. In addition, the multiplying DAC 28 receives the excitation signal generated by oscillator 20 via line 60. In accordance with the well known operation of multiplying DACs, the reference signal is combined with the input excitation signal to produce an output signal, referred to as the precision zero current, that is a scaled version of the input excitation signal. For example, a reference signal having a value half its maximum value would cause the output of the multiplying DAC to be a signal 50% of the input signal. In the present application, multiplying DAC 28 scales the excitation signal of oscillator 20 in accordance with the reference control signal from processor 48. The resultant signal is the precision zero current that is delivered to a null driver 62 over line 64.

The null driver 62 conditions the precision zero current and provides a current boost before sending the precision zero current to the zero winding Z. The precision zero current generates a flux in the zero winding Z that has been engineered to cancel the any remaining differential flux in the core of transformer 32, as detected by sense winding S.

Subsequently, any variations in the concentration of the target gas at the sensor 14 will produce a change in the flux from the active winding A, resulting in a new differential flux. Thus, the flux from the zero winding Z will no longer completely null the flux in the transformer so the sense winding will detect the remaining flux not cancelled. The processor 48 receives a signal indicative of the amount of the remaining flux and then adjusts the control signal so that the precision zero current is likewise adjusted to account for and null the remaining flux. Accordingly, any non-linearity associated with the operation of transformer 32 is eliminated by maintaining the flux within the core of transformer 32 at a minimum.

The control signal is further processed in the processor 48 to generate an actual measured value having the appropriate units which represents the concentration of gas to which the active RTD was exposed. Such processing typically includes digital averaging and correction operations which incorporate other measured parameters such as temperature, pressure and other gas content that may affect the reaction at the active RTD 34. Further, conversion steps are taken in order to convert the value into the appropriate units, such as parts per million (ppm). The conversion operation typically includes multiplying by a scaler value and adding an offset value to account for calibration measurements. The final value calculated by the processor 48 can then be stored on a memory device (not shown) associated with the processor 48 or sent to a display device such as a CRT (not shown).

System calibration typically takes place once a day and comprises the passing of a zero gas (that is, a gas free of the gasses of interest) to the sensing mechanism 14 and measuring a first control signal, and then passing a span gas to the sensing mechanism 14 and then measuring a second control signal. The first and second control signals are then used to devise a linear equation for interpolating raw control signals values generated during normal operation.

When applying the PID algorithm at the processor 48, it is imperative that the input signal be the peak value of the signal received by the sense winding S, or proportional thereto. This is achieved in the following manner. In the preferred embodiment of the present invention, the processor 48 determines a gas concentration level approximately ten times a second, or at one hundredth of the excitation signal, assuming an excitation signal at 1 KHz. Because of the low excitation frequency and the low sampling frequency, it is critical that the ADC 44 samples the signal on line 46 at precise intervals the signal period plus $\pi/2$ (i.e., 90°). If the ADC 44 does sample the signal at the stated interval, then sample at least at the Nyquist frequency (or at twice the excitation frequency). In order to maintain such precise sampling rate, a clock signal is sent from processor 48 to oscillator 20 via line 56 to ensure that the excitation signal remains in phase with the processor sampling rate. Once the sample values are taken, preprocessing is preformed by processor 48 which essentially comprises squaring two consecutive sampled values, adding them together and then taking the square root. This results in a value which is proportional to the peak-to-peak value of the signal in line 50. In addition, the ADC 26 is used to sample the oscillator waveform in order to synchronize the sampling to the oscillator frequency.

2. Circuit Implementation

Figure 3B:
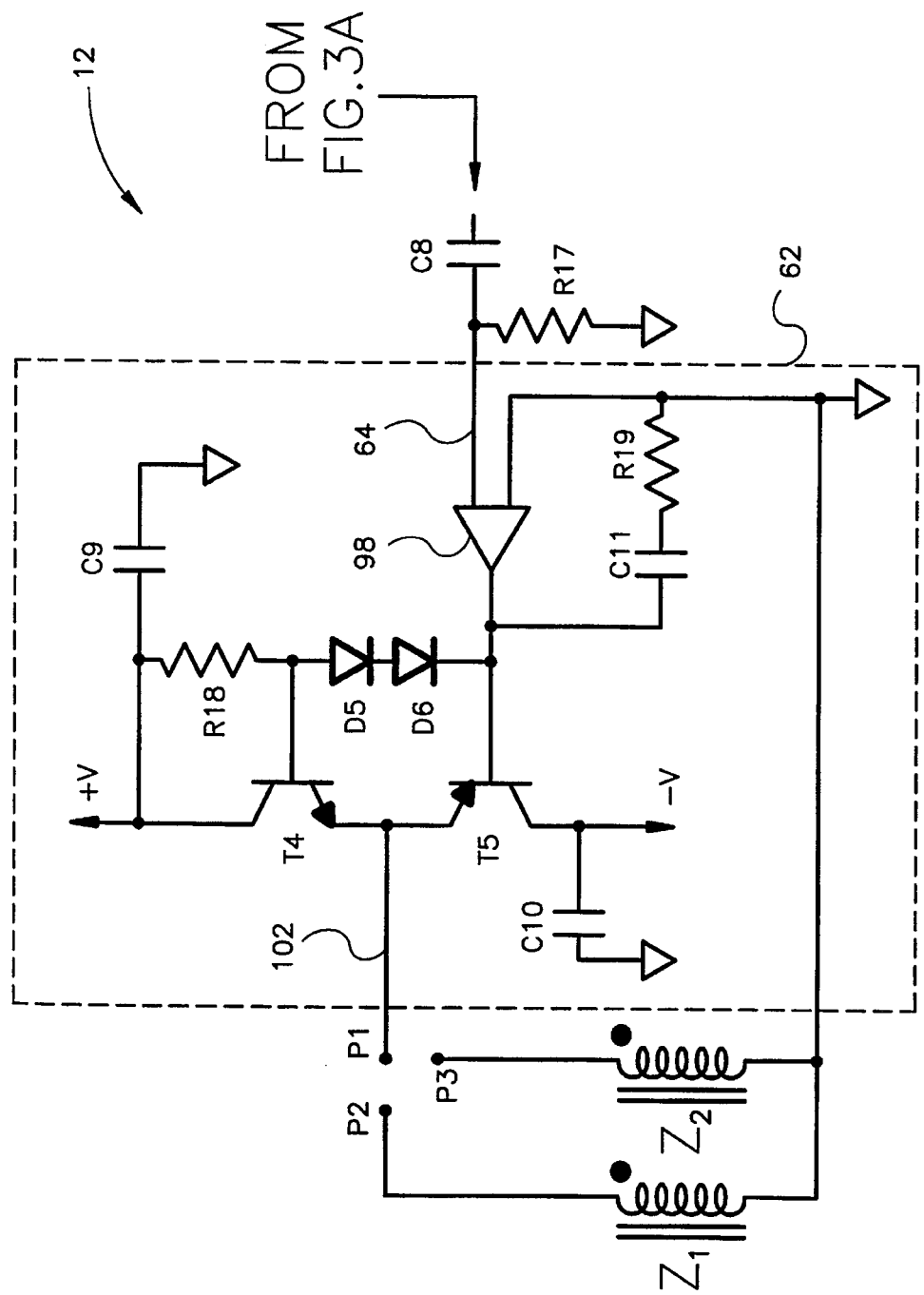
Figure 3C:
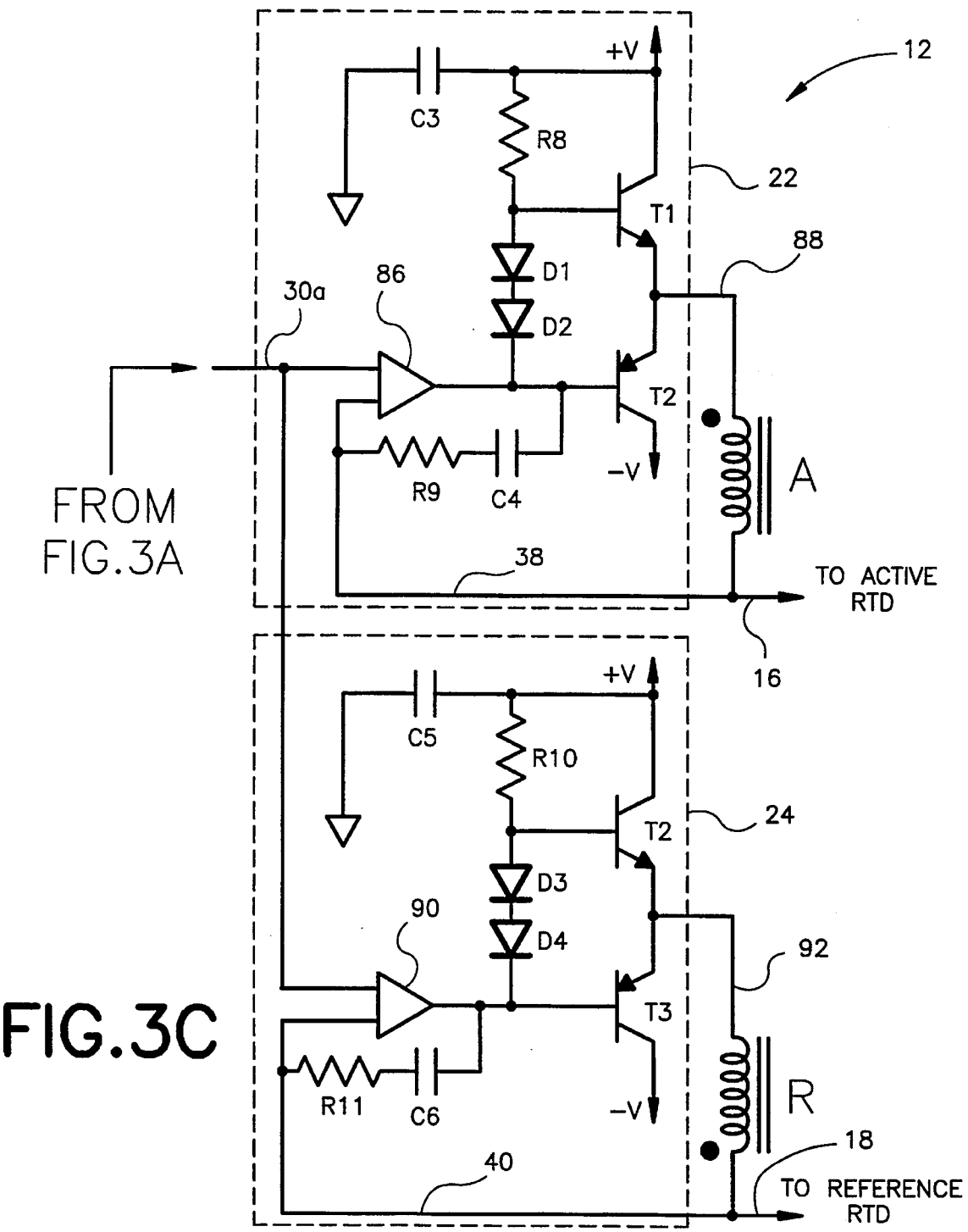

For purposes of illustrating the preferred embodiment of the present invention, an illustrative embodiment of a circuit level implementation of the control mechanism 12 is provided in FIG. 3. It should be understood that the illustrative implementation shown is merely an example of a circuit capable of implementing the present invention, and that numerous other circuit implementations could be employed by one of ordinary skill in the art.

With reference to FIG. 3, oscillator 20 comprises a high purity sine wave oscillator 80 that outputs, on line 30, a 4 volt peak-to-peak wave at a frequency of 1 KHz. The oscillator 20 provides an extremely stable output signal via a phase lock loop circuit that includes a feedback line 82 that is combined with a clock reference signal 56 from the processor 48 at an exclusive-OR gate 84. The output of the exclusive-OR gate 84 is delivered to a very low pass filter comprising an op amp 86, resistor R1, resistor R2, resistor R3, resistor R4, and capacitor C1. The output of the low pass filter is essentially a d.c. voltage having a very slow rate of change. This voltage is sent to an oscillator chip 80 where it corrects for any phase drift in the output signal on line 30 with respect to the clock reference signal on line 56 from the processor 48. Suitable oscillator chips for use with the present invention are commercially available from numerous vendors, such as model XR-2206P manufactured by EXAR, Corporation, San, Calif., U.S.A. A high pass filter comprising a capacitor C2 and a resistor R5 is provided at the output of the oscillator 80 in order to block any d.c. signal on the output line 30.

The output of oscillator 20 is delivered to the active driver 22 and reference driver 24 via lines 30, 30a. It should be noted at this point that active driver 22 and reference driver 24 are substantially identical. For the purpose of brevity, the operation of the active driver 22 will be discussed below in detail with the understanding that reference driver 24 operates in substantially the same manner.

At active driver 22, the oscillator output signal on line 30a is delivered to an op amp 86 having a transistor stage at its output. The transistor stage includes transistors T1 and T2 in conjunction with a capacitor C3, resistor R8, diodes D1 and D2. The transistor stage at the output of the op amp 86 provides a current boost to compensate for the power losses due to the length of lead line 16 (FIG. 2). As a side note, the lead line 16 (and lead line 18) can be configured out of multiple conductors in a parallel configuration in order to reduce the overall resistance, and thus, reduce power loss. In addition, active driver 22 includes an RC feedback loop comprising a resistor R9 and a capacitor C4. The RC feedback loop operates as a high pass filter to stabilize the operation of op amp 86. The output signal of active driver 22 is delivered to the active winding A of transformer 32 (FIG. 2) via line 88. In order to ensure that the voltage cross the active RTD 34 remains constant as its resistance changes, a high input impedance feedback line 38 is provided to connect lead lines 16 and the op amp 86. Consequently, the op amp 86, in conjunction with the transistors T1 and T2, provides an appropriate amount of current over line 88 to the active RTD 34 so that the voltage across it remains constant as its resistance changes due to changes in the temperature of the exhaust and/or due to the exothermic reaction of the catalyst coating with the particular gas of interest.

In substantially the same manner, reference driver 24 provides an output signal over line 92 that varies in order to maintain a constant voltage across reference RTD 36 as its resistance changes due to the change in the temperature of the exhaust. This is achieved in the manner described above through the operation of op amp 90 in conjunction with the transistor stage at its output. The transistor stage includes transistors T2 and T3 in conjunction with a capacitor C5, resistor R10, diodes D3 and D4. In addition, the reference driver 24 includes a feedback loop for the op amp 90 that includes a resistor R11 and a capacitor C6. As with active driver 22, a high input impedance feedback is provided over line 40, connecting lead line 18 to the op amp 90, so that the voltage across the RTD 36 remains constant.

The output signal of reference driver 24 is sent to reference winding R over line 92, creating a flux in the core of the transformer 32 that has an opposite sense with respect to the flux generated by reference winding A. Consequently, the two fluxes cancel out one another in the core of the transformer 32. If the fluxes generated by the active winding A and the reference winding R are not equal because the active RTD 34 has been exposed to the gas of interest which caused a reaction, and thus, a temperature change, a differential flux is generated. Accordingly, whenever the resistance of the active RTD 34 is different from the resistance of the reference RTD 36, the current through line 88 will not equal to the current through line 92, resulting in a differential flux. Combined with this differential flux is a nulling flux from the zero winding Z, as described hereinbefore. The zero winding is configured so that the nulling flux cancels the differential flux. Any remaining flux is detected by the sense winding S.

The current associated with the differential flux in the sense winding S is delivered to the current-to-voltage (I-V) convertor 42 as illustrated in FIG. 3. At the I-V convertor 42, a current loop comprising the sense winding S and a resistor R12 is utilized to generate a voltage proportional to the current in sense winding S. This proportional voltage is taken across the resistor R12 and is sent to an op amp 94. A d.c. offset is provided by the circuit comprising a potentiometer R13, resistor R14, and resistor R15. The d.c. offset is added to the voltage across the resistor R12 to ensure that the output of the I-V convertor 42 is greater than zero. In the preferred embodiment, a 2.5 volt offset is added. Further, the op amp 94 includes a feedback loop comprising a resistor R16 and a capacitor C7 that operates as a low pass filter in order to stabilize the operation of the op amp 94. The output of the I-V convertor 42 is delivered to the ADC 44 via line 46.

The ADC 44 takes the voltage output of the I-V convertor 44 and converts it into a digital signal for processing by the processor 48 sampling the signal on line 46 at a specified frequency, preferable the signal period plus $\pi/2$. Preferably, the ADC 44 is at least a 12 bit convertor which can be implemented with a wide variety of commercially available ADCs. The output of the ADC 44 is sent to processor 48 over line 50.

Processor 48 receives the digital signal from the ADC 44 and processes that signal to produce a control signal directly proportional to the concentration of the gas of interest in the exhaust flow, as detected by the sensor mechanism 14. It is this control signal that is both delivered to the multiplying DAC 28 over line 58 and further processed in order to provide an actual concentration measurement of the appropriate units. A suitable processor for implementing the processor 48 is the processor model 80C186EB manufactured by Intel, Corporation, Santa Clara, Calif., U.S.A., though it can be appreciated by one skilled in the art that numerous other processors which are commercially available would likewise be suitable for implementing processor 48.

Processor 48 performs essentially three operations. First, processor 48 clocks the ADC 44 at precise sampling intervals so that consecutive sampling values are taken at the signal period plus $\pi/2$. Then two consecutive sampled values are squared, combined and the square root taken in order to provide a value proportional to the peak value of the waveform on line 50. This preprocessing is performed because a peak value must be used in the subsequent application of the PID algorithm. The processor 48 is able to clock the ADC 44 at a constant sampling rate, preferably at the signal period plus $\pi/2$, by utilizing the reference oscillator signal provided by the ADC 26 over line 52. As mentioned above, the ADC 26 receives the excitation signal generated by oscillator 20 and indicates to the processor 48 over line 52 whether the phase of the waveform on line 50 is positive or negative. In addition, the processor 48 is kept in phase with the output of oscillator 20 via the reference signal sent over fine 56 to oscillator 20, as described above. Thus, by sampling at the same phase, the effects of harmonics is reduced.

Secondly, once the preprocessing has been performed, a PID algorithm is applied to the proportional peak value in order to determine a control signal. Once the control signal has been determined by the PID algorithm, the control signal is sent to the multiplying DAC 28 via line 58. In addition, the control signal is further processed in order to produce the an actual measurement value that may be stored in memory or sent to a display screen such as a CRT, as discussed hereinbefore.

The multiplying DAC 28 both receives the control signal from the processor 48 and the excitation signal from the oscillator 20 via fines 30, 30c. The multiplying DAC 28 essentially multiplies the two signals in order to produce a resultant precision zero signal that is a scaled version of the excitation signal from the oscillator 20. The control signal essentially operates as a reference signal that indicates the portion of the excitation signal that is to be delivered to the zero winding Z to cancel the differential flux detected by the sense winding S. A suitable multiplying DAC for implementing multiplying DAC 28 of the present invention is Model DAC-312, manufactured by Precision Monolithics, Inc., Santa Clara, Calif., U.S.A., though it can be appreciated by one skilled in the art that numerous other multiplying DACs that are commercially available are likewise suitable for implementing multiplying DAC 28. The multiplying DAC cited above is a 12 bit DAC which provides 4096 possible values, or a resolution of 0.024. However, the actual system resolution is typically less due to the margin of error in the manufacture of the electrical components and various environmental factors that may vary the performance of analog components. Nevertheless, it is recognized that the overall accuracy of the control mechanism 12 is principally dependent upon the accuracy of the multiplying DAC 28 that provides the nulling signal to the zero winding Z.

The output of the multiplying DAC 28 is sent to a high pass filter comprising a capacitor C8 and a resistor R17 in order to block any d.c. signal from being sent to the null driver 62.

The null driver 62, as illustrated in FIG. 3, is configured substantially the same as active driver 22 and reference driver 24. The null driver 62 receives the output of the multiplying DAC 28 after it passes through the high pass filter via line 64. Line 64 delivers the nulling signal to an op amp 98. At the output of the op amp 98 is a transistor stage comprising the transistors T4, T5 in conjunction with a capacitor C9, resistor R18, diode D5, diode D6, and capacitor C10. As with the active driver 22 and reference driver 24, the transistor stage provides a predetermined amount of current boost to the precision zero signal that is subsequently sent to the zero winding Z. A feedback loop that comprises a capacitor C11 and a resistor R19 is provided with the op amp 98 in order to stabilize the operation thereof. The output of null driver 62 is then sent to the zero winding Z (FIG. 2). As shown in FIG. 3, the zero winding Z may comprise the option of one or more transformer windings with different turn ratios.

For purposes of illustrating the present invention, the circuit in FIG. 3 provides the option between zero winding $Z_1$ and zero winding $Z_2$. The zero winding $Z_1$ has a 1:1 winding ratio with respect to the windings A, R, and S of transformer 32. The alternative zero winding, $Z_2$, has a 20:1 winding ratio with respect to windings A, R, and S of transformer 32. In the preferred embodiment, a jumper is hardware between either pins P1 and P2 or between pins P1 and P3 in order to implement the preferred zero winding for the particular application of the system 10. The zero winding $Z_2$ provides the user with the option of increasing the dynamic range of the nulling signal, and thus, increasing the span of concentration values for which the system 10 is sensitive. The downside to incorporating the zero winding $Z_2$ is that it provides less resolution in the nulling signal. However, this may be compensated for by providing a multiplying DAC 28 with greater resolution, for instance, a 16 bit multiplying DAC.

Accordingly, the output of null driver 62 is sent over line 102 to the preferred zero winding Z (i.e., $Z_1$ or $Z_2$) and produces a cancelling flux that has an opposite sense to the differential flux detected by winding S such that the cumulative flux in the core of transformer 32 is zero. By keeping the cumulative core flux of transformer 32 to a minimum, preferably zero, the non-linearity of transformer 32 does not introduce noise or error in operation of the measuring system 10.

It should be noted that more than one sensor mechanism 14 can be supported by one oscillator 20 and processor 48 of control mechanism 12. By providing a transformer and associated drivers and converters for each sensor mechanism 14, multiple sensor mechanisms 14 can be incorporated into a single measuring system so as to simplify circuit implementation, reduce system cost, and enable more efficient modifications and/or changes to the operation of measuring system 10.

3. Operation

In operation, oscillator 20 generates a stable 4 volt peak-to-peak excitation signal at a frequency of 1 KHz over line 30 which is sent to active driver 22 and reference driver 24. Both the active driver 22 and reference driver 24 operate to maintain a constant voltage over active RTD 34 and reference RTD 36, respectively. This is accomplished by varying the current delivered by the respective drivers 22, 24 to their corresponding RTDs 34 and 36, respectively. Thus, as the resistances of the active RTD 34 and reference RTD 36 vary with changes in the temperature of the exhaust, the respective driver circuits 22, 24 produce a proportional change in a current such that the voltage across the RTDs 34, 36 remains constant. Any variations from manufacturing error which might affect the resistance of the respective RTDs is accounted for through the calibration of the measuring system 10, typically performed on a daily basis. The information gathered during calibration is incorporated into the control signal at processor 48 during the post processing performed therein.

When the active RTD 34 is exposed to the particular gas of interest, the catalyst coating thereon reacts, causing the temperature of the active RTD 34 to vary with reference to the reference RTD 36, and thus, causes the active driver 22 to deliver a proportional amount of current to active RTD 34 so that the voltage across the active RTD 34 remains constant and equal to the voltage across the reference RTD 36. Accordingly, different currents are now passing through the active winding A and the reference winding R of the transformer 32. Because the active winding A and the reference winding R are configured with opposite senses, the flux generated by the respective windings cancel out one another so as to produce a resultant, differential flux in the core of transformer 32 which is detected by sense winding S. A current associated with the flux detected by sense winding S is converted into a voltage value by the I-V convertor 42 so that it can be subsequently converted into a digital signal by the ADC 44. By taking the analog signal and converting it into a digital signal, the control mechanism 12 minimizes the sensitivity of system 10 to electrical noise, such as EMF and RFI noises, found at most industrial facilities. Further, by converting the signal from analog-to-digital, the effect of drift resulting from temperature variations and the aging of the electrical components is reduced. Free from the aforementioned effects, the digital signal is more accurate which results in a more sensitive monitoring system 10.

The digital signal from the DAC 44 is received by the processor 48 where it undergoes preprocessing operations. The preprocessing operation includes determining a proportional peak-to-peak value of the signal using two consecutive sampled values. The proportional peak-to-peak value is then processed using a PID algorithm in order to determine a precision null current or control signal which is indicative of the concentration of the particular gas of interest present in the exhaust stream. The control signal then undergoes postprocessing including digital averaging, corrections based upon other measured parameters such as temperature, pressure, or moisture content of the exhaust, and the calibration factors, and lastly, conversions of the value to the appropriate units.

At substantially the same time, the control signal is also delivered to the multiplying DAC 28 where it is combined with the excitation signal from the oscillator 20 in order to produce a precision zero signal. This zero signal is delivered to the null driver 62 where it passes through the op amp 98 and the associated transistor stage in order to buffer the signal and provide a current boost. The zero signal is subsequently delivered to zero winding Z where it produces a nulling flux that has an opposite sense to the flux detected by sense winding S. In an ongoing fashion, the cumulative flux within transformer 32 is maintained at substantially zero by updating the control signal on a continuous basis (for example, ten times every second) in order to generate a nulling flux equal to the differential flux detected by sense winding S.

In concluding the detailed description, it should be noted that it will be obvious to those skilled in the art that many variations and modifications may be made to the preferred embodiment without substantially departing from the principles of the present invention. All such variations and modifications are intended to be included herein within the scope of the present invention, as set forth in the following claims. Further, in the claims hereafter, the structures, materials, acts, and equivalents of all means or step plus function elements are intended to include any structures, materials, or acts for performing the functions.

Wherefore, the following is claimed:

1. A measuring system for use in an emission monitor for measuring emissions from a process comprising:

a sensor having an active resistance temperature device (RTD) and a reference RTD;

an oscillator for generating an excitation signal:

a transformer having an active winding, a reference winding, a sense winding, and a zero winding;

said active winding connected to said active RTD configured to receive a portion of said excitation signal at a first current so as to produce a first flux, said first current also passing through said active RTD and varying proportionally with changes in a first resistance of said active RTD so that a first voltage across said active RTD remains substantially constant;

said reference winding connected to said reference RTD and configured to receive a portion of said excitation signal at a second current so as to produce a second flux, said second current also passing through said reference RTD and varying proportionally with changes in second resistance of said reference RTD so that a second voltage across said reference RTD remains substantially constant, and wherein said first and second fluxes have opposite senses so as to cancel one another in said transformer when said first and second fluxes are equal;

said sense winding configured to detect a sense flux in said transformer;

a current-to-voltage converter connected to said sense winding and configured for transforming a current produced in said sense winding by said sense flux into a voltage;

an analog-to-digital converter connected to said current-to-voltage converter and configured for transforming said voltage output from said current-to-voltage converter into a digital signal;

a processor connected to said analog-to-digital converter and configured for processing said digital signal into a control signal in accordance with a programmed algorithm;

a multiplying digital-to-analog converter (DAC) for receiving a signal from said oscillator and said control signal from said processor, and outputting a nulling signal from said oscillator based upon said control signal; and said zero winding configured to receive said nulling signal and generating a nulling flux to cancel said sense flux so as to minimize drift and non-linearity of said transformer;

wherein said control signal is combined in said processor with measured parameter values and calibration factors to determine an emission level value.

2. The system of claim 1, further comprising an active driver associated with said active winding and a reference driver associated with said reference winding for boosting said first and second currents, respectively, for enabling said active and reference RTDs to be located remotely from said transformer.

3. The system of claim 1, further comprising an active driver associated with said active RTD and a reference driver associated with said reference RTD, said active and reference drivers configured to maintain substantially equal and substantially constant voltages across said active RTD and said reference RTD, respectively.

4. The system of claim 1, further comprising a null driver for stabilizing said nulling signal from said multiplying DAC.

5. The system of claim 1, wherein said zero winding has a different number of windings from said active, reference and sense windings in order to adjust resolution of said nulling signal.

6. The system of claim 1, further comprising a second analog-to-digital converter for transforming said signal from said oscillator into a digital phase signal that is sent to said processor as a phase indicator of said excitation signal.

7. The system of claim 1, wherein said processor updates said control signal once every 0.1 seconds.

8. The system of claim 1, wherein said measure parameter values include temperature, pressure, and humidity.

9. The system of claim 1, wherein said processor includes a PID algorithm for processing said digital signal.

10. The system of claim 1, wherein said multiplying DAC has at least 12 bit resolution.

11. A measuring system for measuring emissions from an industrial process, comprising:

a sensor mechanism including an active resistive temperature device (RTD) and a reference RTD;

a control mechanism connected to said sensor mechanism and configured for measuring a difference in currents through said active and reference RTDs, said control mechanism including an oscillator for generating an excitation signal that is delivered to said sensor mechanism, a four-winding transformer for detecting a remaining flux in a sense winding of said transformer by combining a differential flux associated with said difference in currents through said RTDs and a nulling flux to determine a differential signal via transformer flux cancellation in a summing core of said transformer, processor means for processing said differential signal into a control signal indicative of a concentration of an emission of interest sensed by said sensor mechanism, nulling means for generating said nulling flux from said control signal in order to cancel said remaining flux in said transformer by introducing a nulling signal into a null winding of said transformer; and wherein said control signal is used to determine an emission value.

12. The system of claim 9, further comprising a driver associated with each of said active and reference RTDs for boosting said first and second currents for enabling said RTDs to be located remotely from said summing core.

13. The system of claim 11, further comprising a driver associated with each of said active and reference RTDs for maintaining substantially equal and substantially constant voltages across said active RTD and said reference RTD.

14. The system of claim 11, where said processor means includes a PID algorithm for processing said differential signal.

15. The system of claim 11, wherein said processor means includes signal conditioning circuitry for converting said differential signal into a digital signal for processing.

16. The system of claim 11, wherein said nulling means includes a multiplying digital-to-analog converter.

17. A method for measuring emissions of a process, comprising the steps of:

introducing a catalytic heat sensor into an exhaust flow of said process, said catalytic heat sensor including an active resistive temperature device (RTD) and a reference RTD;

measuring a first current through said active RTD and a second current through said reference RTD when voltages across said active RTD are approximately equal;

determining a differential signal between said first and second currents by passing said currents through a first winding and a second winding, respectively, of a four winding transformer in which said first and second windings have opposite winding senses, thereby producing a differential flux;

combining said differential flux and a nulling flux to determine a sense flux in a third winding of said transformer, said sense flux producing said differential signal in said third winding;

processing said differential signal with filter means to generate a control signal;

processing said control signal into an actual value of a target gas of interest;

determining a nulling signal based upon said control signal, and providing said nulling signal to a fourth winding in order to cancel out said differential flux.

18. The method of claim 17, further including the step of boosting said first and second currents to enable said active and reference RTDs to be located remotely with respect to said transformer.

19. The method of claim 17, further including the step of converting said differential signal into a digital signal prior to applying said filter means.

20. The method of claim 17, wherein said filter means includes a PID algorithm.

* * * * *